US007186839B2

(12) United States Patent
Jones et al.

(10) Patent No.: US 7,186,839 B2
(45) Date of Patent: Mar. 6, 2007

(54) CHEMICAL PROCESS FOR THE EXTRACTION OF 2-HYDROXY PYRIDINE DERIVATIVES, 2-HYDROXYQUINOLINE, AND 2-HYDROXYBENZOTHIAZOLE

(75) Inventors: Raymond Vincent Heavon Jones, Stirlingshire (GB); Joanne Emma Murray, Stirlingshire (GB); Jennifer Ann White, Stirlingshire (GB); Alastair Iain Currie Stewart, Stirlingshire (GB); Susan Thomson Hamilton, Stirlingshire (GB); Alan John Whitton, Stirlingshire (GB); Julie Forrester, Stirlingshire (GB)

(73) Assignee: Syngenta Limited, Guildford (GB)

( * ) Notice: Subject to any disclaimer, the term of this patent is extended or adjusted under 35 U.S.C. 154(b) by 0 days.

(21) Appl. No.: 10/332,105

(22) PCT Filed: Jun. 14, 2001

(86) PCT No.: PCT/GB01/02625

§ 371 (c)(1),
(2), (4) Date: Jul. 14, 2003

(87) PCT Pub. No.: WO02/02528

PCT Pub. Date: Jan. 10, 2002

(65) Prior Publication Data
US 2004/0099609 A1 May 27, 2004

(30) Foreign Application Priority Data
Jul. 3, 2000 (GB) ................... 0016338.6

(51) Int. Cl.
A61K 31/44 (2006.01)
A61K 31/47 (2006.01)
A61K 31/428 (2006.01)
C07D 215/18 (2006.01)
C07D 213/61 (2006.01)
C07D 277/68 (2006.01)

(52) U.S. Cl. .............. 546/153; 546/153; 546/303; 548/209; 514/312; 514/345; 514/367

(58) Field of Classification Search ........ 546/303, 546/153; 548/209; 514/312, 345, 367
See application file for complete search history.

(56) References Cited

U.S. PATENT DOCUMENTS 3,355,456 A 11/1967 Sexton
3,609,158 A * 9/1971 Torba .................. 546/302
4,208,280 A 6/1980 Naylor
4,370,483 A 1/1983 Papenfuhs
5,801,241 A 9/1998 Lim et al.

FOREIGN PATENT DOCUMENTS

| GB | 2305174 | 4/1997 |
| JP | 58154561 | 9/1983 |
| WO | 9729088 | 8/1997 |
| WO | WO-98-40355 A1 | 9/1998 |
| WO | WO-00-14068 A1 | 3/2000 |

OTHER PUBLICATIONS

Shiao, Min Jen et al. "Demethylation of methoxypyridines with sodium trimethylsilanethiolate." Heterocycles (1993), 36(2), 323-8.*
G.R. Newkome et al., "Chemistry of Heterocyclic Compounds. 17. Improved Synthesis of 2-pyridones." Synthesis (1974), vol. 10, p. 707.*
Patent Abstracts of Japan, vol. 007, No. 277 (C-199), Dec. 9, 1983.
Shiao, Min Jen et al., "Demethylation of Methoxpyridines With Sodium Trimethylsilanethiolate", HETEROCYCLES (1993), 36(2), 323-8, examples 2E, 2F.
G.R. Newkome et al., "Chemistry of Heterocyclic Compounds, 17, Improved Synthesis of 2-Pyridones", SYNTHESIS, vol. 10, 1974, p. 707.
Ya. I. Korenman, Russian Journal of Applied Chemistry, vol. 71, No. 3 (1998), p. 532-534.

* cited by examiner

Primary Examiner—Joseph K. McKane
Assistant Examiner—Janet L. Coppins
(74) Attorney, Agent, or Firm—Rebecca A. Gegick

(57) ABSTRACT

A process for extracting from aqueous solution the alkali metal or calcium salt of a halo or haloalkyl substituted 2-hydroxypyridine, or a 2-hydroxyquinoline or 2-hydroxybenzothiazole which comprises contacting an aqueous alkaline or neutral solution of the alkali metal or calcium salt, in which is dissolved an alkali metal fluoride, chloride, bromide, hydroxide, sulphate, sulphite, cyanate, cyanide, thiocyanate, thiosulphate, sulphide, phosphate, hydrogen phosphate, carbonate, bicarbonate, borate, chlorate, hypochlorite, perchlorate, nitrite, chromate, dichromate or permanganate or calcium chloride, bromide, nitrate, nitrite, chlorate, hypochlorite, perchlorate, thiocyanate, thiosulphate, chromate, dichtromate or permanganate, with a partially water-miscible organic solvent so as to transfer aqueous solution of the alkali metal or calcium salt of the 2-hydroxypyridine, 2-hydroxyquinoline or 2-hydroxybenzothiasole into the solvent whilst retaining separate aqueous and solvent phases, and thereafter separating the solvent phase containing the alkali metal or calcium salt and water from the aqueous phase, the ratio of solvent to water in the separated solvent phase being from 0.5:1 to 10:1 w/w.

10 Claims, No Drawings

CHEMICAL PROCESS FOR THE EXTRACTION OF 2-HYDROXY PYRIDINE DERIVATIVES, 2-HYDROXYQUINOLINE, AND 2-HYDROXYBENZOTHIAZOLE

This invention relates to a chemical process and more particularly to a process for extracting organic salts from aqueous solutions.

Heteroaromatic ethers, for instance aralkyl heteroaryl ethers, may be prepared by the Williamson ether synthesis. This involves the reaction of a metal salt of a heteroaryl hydroxide with an aralkyl halide in an organic solvent. The metal salt of the heteroaryl hydroxide may be prepared prior to reaction or in situ, i.e. by reacting the heteroaryl hydroxide with the aralkyl halide in the presence of a metal base.

The heteroaryl hydroxide may be prepared by the hydrolysis of a heteroaryl halide using an aqueous metal base. In this case it is usual to acidify the resulting aqueous solution of the metal salt of the heteroaryl hydroxide to precipitate the heteroaryl hydroxide. The heteroaryl hydroxide is then isolated and dried, and the metal salt reformed in the synthesis solvent either before or during reaction with the aralkyl halide.

It has now been found that the metal salt of a heteroaryl hydroxide can be extracted from the hydrolysis reaction mixture and used directly in the ether synthesis without the need for acidification, isolation of the hydroxide and reformation of the metal salt. This makes for a more efficient and simpler manufacturing process, avoiding an extra acidification and isolation step.

Cyclohexanone is known to be used to extract certain organic material from aqueous media (see for example U.S. Pat. No. 5,801,241 and U.S. Pat. No. 4,208,280). An article by Ya. I. Korenman et al in the *Russian Journal of Applied Chemistry*, Vol. 71, No. 3 [1998], 532–534, discusses the extraction of phenol with cyclohexanone from aqueous salt solutions and indicates that the most efficient extraction is achieved at a pH of about 2.

Thus, according to the present invention, there is provided a process for extracting from aqueous solution the alkali metal or calcium salt of a halo or haloalkyl substituted 2-hydroxypyridine, or a 2-hydroxyquinoline or 2-hydroxybenzothiazole which comprises contacting an aqueous alkaline or neutral solution of the alkali metal or calcium salt, in which is dissolved an alkali metal fluoride, chloride, bromide, hydroxide, sulphate, sulphite, cyanate, cyanide, thiocyanate, thiosulphate, sulphide, phosphate, hydrogen phosphate, carbonate, bicarbonate, borate, chlorate, hypochlorite, perchlorate, nitrite, chromate, dichromate or permanganate or calcium chloride, bromide, nitrate, nitrite, chlorate, hypochlorite, perchlorate, thiocyanate, thiosulphate, chromate, dichromate or permanganate, with a partially water-miscible organic solvent so as to transfer aqueous solution of the alkali metal or calcium salt of the 2-hydroxypyridine, 2-hydroxyquinoline or 2-hydroxybenzothiazole into the solvent whilst retaining separate aqueous and solvent phases, and thereafter separating the solvent phase containing the alkali metal or calcium salt and water from the aqueous phase, the ratio of solvent to water in the separated solvent phase being from 0.5:1 to 10:1 w/w.

The choice of solvent is determined by its ability to extract sufficient of the aqueous solution of the alkali metal or calcium salt of the 2-hydroxypyridine, 2-hydroxyquinoline or 2-hydroxybenzothiazole such that the ratio of solvent to water in the separated solvent phase is from 0.5:1 to 10:1 w/w, for example from 0.5:1 to 5:1 w/w and typically from 0.5:1 to 3:1 w/w.

The solvent water ratio is readily determined by standard analytical techniques. Thus, the water content of the separated solvent phase can be measured using a Metrohm 784 KFP Titrino (supplied by Metrohm Ltd CH-9101 Herisau Switzerland) incorporating Hydranal-Composite 5K and Hydranal-Ketosolver reagents. These reagents are supplied by Riedel-de Haen Laborchemikalien GmbH and Co KG, Postfach/PO Box 10 02 62, F-30918 Seelze, Germany. The salt content can be measured by a standard titration with hydrochloric acid and the solvent content can then be calculated by difference.

Suitable solvents include those solvents which can dissolve from 1 to 50% w/w, for example from 1 to 30% w/w of water. They include alcohols such as n-butanol, 2-methyl-1-propanol, t-amyl alcohol and iso-butyl alcohol, ketones such as methyl ethyl ketone (MEK) and 4-methyl-2-pentanone (MIBK), ethers such as diethyl ether, alkyl alkanoates such as ethyl acetate and cycloalkanones.

Suitable cycloalkanones include cyclopentanone, cyclohexanone and cycloheptanone and alkyl-substituted cycloalkanones such as 2- and 3-methylcyclopentanone, 2,2- and 2,4-dimethylcyclopentanone, 2-, 3- and 4-methylcyclohexanone, 2,2- and 2,6-dimethylcyclohexanone, 2,2,6-trimethylcyclohexanone, 4-ethylcyclohexanone, 2-tert-butylcyclohexanone, 4-tert-butylcyclohexanone. Unsubstituted $C_{5-7}$ cycloalkanones are preferred, especially unsubstituted cyclohexanone. The quantity of solvent used will normally be 1 to 8 moles, for example 1 to 6 moles, typically 4 moles, for each mole of the alkali metal or calcium salt of the 2-hydroxypyridine, 2-hydroxyquinoline or 2-hydroxybenzothiazole present.

The 2-hydroxypyridine is substituted with a halogen atom, for example a chlorine atom or a fluorine or bromine or iodine atom, or a haloalkyl group such as a halo($C_{1-4}$) alkyl group, especially a trifluoromethyl or difluoromethyl group. The substituent may be in any position on the pyridine ring but is preferably in the 5- to 6-position. Examples of suitable 2-hydroxypyridines are 6-chloro-2-hydroxypyridine, 5-trifluoromethyl-2-hydroxypyridine, 6-difluoromethyl-2- hydroxypyridine and especially 6-trifluoromethyl-2-hydroxypyridine.

Without wishing to be bound by any theory, it is believed that the electron withdrawing nature of the substituent and its position on the 2-hydroxypyridine ring should be such as to encourage salt formation at the oxygen atom rather than at the nitrogen atom of the hydroxypyridine/pyridone ring.

Alkali metals include lithium, sodium and potassium. Sodium and potassium are preferred for both the alkali metal salt of the 2-hydroxypyridine etc., and the alkali metal fluoride, etc. Potassium is especially preferred.

The alkali metal fluoride, chloride, bromide, hydroxide, sulphate, sulphite, cyanate, cyanide, thiocyanate, thiosulphate, sulphide, phosphate, hydrogen phosphate, carbonate, bicarbonate, borate, chlorate, hypochlorite, perchlorate, nitrite, chromate, dichromate or permanganate, or calcium chloride, bromide, nitrate, nitrite, chlorate, hypochlorite, perchlorate, thiocyanate, thiosulphate, chromate, dichromate or permanganate, which is dissolved in the aqueous alkaline or neutral solution of the metal salt of the 2-hydroxypyridine, etc. is required to effect separation of the aqueous and organic phases and increase extraction efficiency. Suitably it is a sodium or potassium fluoride, chloride, bromide, sulphate or phosphate or calcium chloride.

Where the metal salt of the 2-hydroxypyridine is obtained by the hydrolysis of the corresponding fluoride or chloride using a metal base, such as sodium or potassium hydroxide, alkali metal halide is formed in situ as a by-product of the hydrolysis and no additional inorganic salt may be necessary. However, further alkali metal fluoride, etc., either the same as that formed in situ or different, may be added if desired.

The cation of the alkali metal fluoride etc., may be the same as or different from the cation of the alkali metal or calcium salt of the 2-hydroxypyridine, etc., but will often be the same. When a different cation is used, cation exchange may occur.

The amount of alkali metal fluoride etc. used will normally be at least 0.5 mole and up to 2 mole, usually about 1.0 mole, for each mole of the alkali metal or calcium salt of the 2-hydroxypyridine, etc., present.

The aqueous solution of the alkali metal or calcium 2-hydroxypyridine, 2-hydroxyquinoline or 2-hydroxybenzothiazole may be prepared by treating the 2-hydroxy pyridine, etc., with an alkali metal or calcium hydroxide in water with or without the alkali metal or calcium fluoride, etc., present. If not present, it may be added afterwards. Alternatively, the alkali metal or calcium salt of the 2-hydroxypyridine, etc., may be preformed. In this case, the aqueous solution may be kept neutral or made alkaline by the addition of a base, such as an alkali metal or calcium hydroxide or alkali metal carbonate.

Where the alkali metal or calcium salt of the 2-hydroxypyridine is obtained by the hydrolysis of the corresponding 2-halopyridine using an alkali metal or calcium base and is to be extracted directly from the aqueous hydrolysis medium, the aqueous solution may already be alkaline. However, further base, either the same as that used for the hydrolysis or different, may be added if desired.

In one aspect of the present invention there is provided a process for extracting from aqueous solution the alkali metal salt of 6-trifluoromethyl-2-hydroxypyrinidine, which comprises contacting an alkaline aqueous solution of the alkali metal salt, in which is dissolved an alkali metal fluoride, chloride, bromide, sulphate or phosphate, with a cycloalkanone, so as to transfer the alkali metal salt into the cycloalkanone, and thereafter separating the cycloalkanone containing the alkali metal salt from the aqueous solution.

The process of the invention is conveniently carried out by adding the organic solvent to the aqueous alkaline or neutral solution of the alkali metal or calcium salt of the 2-hydroxypyridine, etc., containing the alkali metal fluoride, etc., or vice versa, stirring or otherwise agitating the two-phase system until no further salt is extracted into the organic solvent phase and separating the two phases. The extraction can be carried out effectively at atmospheric pressure and at a temperature of from 0° C., to 90° C., normally from 15° C. to 80° C., for example from 20° C. to 70° C., especially from 50° C. to 70° C., and typical at about 60° C., depending on the boiling point of the solvent. The optimum agitation time will depend on the quantity of solution to be extracted, the amount of solvent used to carry out the extraction, the temperature and the efficiency of agitation. For example, for small scale preparations where the alkali metal or calcium salt is extracted from 5 to 20 moles of water, 30 minutes stirring at 40° C. to 80° C. using 1 mole of the solvent to 2 to 6 moles of water is usually sufficient to extract 90% or more of the alkali metal or calcium salt.

The examples presented later show how the extraction can be done batch-wise but it will be apparent that it may also be done by continuous or counter-current extraction using standard chemical processing techniques.

The invention process is of particular interest in the extraction of alkali metal salts, especially potassium salts, of 6-trifluoromethylpyridone obtained by the hydrolysis of 2-fluoro- or 2-chloro-6-trifluoromethylpyridine using an alkali metal hydroxide. 6-Trifluoromethylpyridone is a useful intermediate in the preparation of, for instance, agrochemical products and is conveniently extracted as the metal salt direct from the hydrolysis reaction medium using the present invention for further processing. The hydrolysis of 2-chloro-6-trifluoromethylpyridine and of 2-fluoro-6-trifluoromethylpyridine and mixtures thereof using an aqueous alkali metal hydroxide is described in WO 98/40355 and WO 00/14068.

The invention is illustrated by the following Examples in which:

| | |
|---|---|
| g = grammes | GC = gas chromatography |
| mol = moles | ° C. = degrees centigrade |

EXAMPLE 1

This example illustrates the extraction of the sodium salt of 6-trifluoromethyl-2-hydroxypyridine from an aqueous solution containing potassium fluoride produced in situ, into cyclohexanone at 80° C.

2-Fluoro-6-trifluoromethylpyridine (50.0 g at 99.0% strength, 0.3 mol), potassium hydroxide flake (39.3 g at 95.0% strength, 0.666 mol) and water (40.0 g, 2.222 mol) were charged to a 500 ml round bottom flask and the mixture heated to 110° C. with agitation. The reaction mixture was held at this temperature for 4 hours before cooling to 80° C. Cyclohexanone (117.6 g, 1.2 mol) was added to the cooled reaction mixture and the aqueous and organic layers were stirred at 80° C. for 30 minutes before being allowed to settle. The lower aqueous layer was run off and the organic layer containing 29.8% of 6-trifluoromethyl-2-hydroxypyridine potassium salt (93.3% yield) was isolated.

EXAMPLE 2

This example further illustrates the extraction of the potassium salt of 6-trifluoromethyl-2-hydroxypyridine from an aqueous solution containing potassium fluoride produced in situ into cyclohexanone at 80° C.

Potassium hydroxide flake (175.1 g at 95% strength, 2.97 mol) and water (175.1 g, 9.73 mol) were charged to a 1 liter round bottom flask fitted with a condenser, agitator and contents thermometer. The contents were stirred to give a solution. The solution was heated to 130° C. (reflux).

2-Fluoro-6-trifluoromethylpyridine (224.5 g at 99.2% strength, 1.35 mol) was added dropwise over 1 hour maintaining a gentle reflux and a temperature of greater than 120° C. The temperature was held for a further 4 hours and the reaction tested. The end of reaction test showed 0.3% starting material and 99.7% product by area GC.

The reaction was cooled to 95° C. and cyclohexanone was added. After stirring at 80° C. for 30 minutes agitation was stopped and the two layers allowed to settle for 30 minutes. The lower aqueous layer was run off and the cyclohexanone solution containing the potassium salt of 6-trifluoromethyl-2-hydroxypyridine was collected for further processing.

EXAMPLE 3

This example illustrates the extraction of the potassium salt of 6-trifluoromethyl-2-hydroxypyridine from an aqueous solution containing potassium fluoride produced in situ into cyclohexanone at 60° C.

Aqueous potassium hydroxide solution (from 19.5 g KOH at 95% strength containing 0.98 g water, and 36 g water) was stirred at 100° C., before the first of five equal portions of 2-fluoro-6-trifluoromethylpyridine (total weight 25 g at 99% strength, 0.15 mol) was added. An exotherm to 110° C. was observed, and reaction temperature was returned to 100° C. before subsequent portions of the pyridine were added. The reaction was stirred for 1 hour after the final portion of pyridine was added. The total reaction time was approximately 3.5 hours. Analysis by GC confirmed that the reaction had reached completion. The mixture was then cooled to 60° C. before cyclohexanone (58.8 g) was added, and the mixture stirred for 30 minutes. The two layers formed were separated to give a cyclohexanone solution of 6-trifluoromethyl-2-hydroxypyridine potassium salt and an aqueous waste.

EXAMPLE 4

This example illustrates the extraction of the potassium salt of 6-trifluoromethyl-2-hydroxypyridine from an aqueous solution containing added potassium fluoride, into cyclohexanone at 60° C.

A solution of potassium hydroxide (3.1 g at 95% strength, 0.05 mol), 6-trifluoromethyl-2-hydroxypyridine (7.1 g, 0.04 mol) and potassium fluoride (2.3 g, 0.04 mol) in water (7.8 g), was stirred at 60° C. for one hour. Cyclohexanone (17.2 g, 0.18 mol) was then charged and the solution was stirred for a further 30 min at 60° C.

The solution was transferred to a heated separating funnel where it was allowed to separate into two clear phases. The lower substantially aqueous phase was separated (7.59 g), followed by the upper substantially organic phase (30.82 g). By quantitative analysis it was shown that >99% of the potassium salt of 6-trifluoromethyl-2-hydroxypyridine was extracted into the organic cyclohexanone phase.

In a similar fashion, >99% of the potassium salt of 6-trifluoromethyl-2-hydroxypyridine extracted using cyclopentanone.

EXAMPLE 5

This example illustrates the extraction of the potassium salt of 6-trifluoromethyl-2-hydroxypyridine from an aqueous solution containing added potassium chloride into cyclohexanone at 60° C.

A solution of potassium hydroxide (3.1 g at 95% strength, 0.05 mol), 6-trifluoromethyl-2-hydroxypyridine (7.1 g, 0.04 mol) and potassium chloride (2.95 g, 0.04 mol) in water (7.8 g), was stirred at 60° C. for one hour. Cyclohexanone (17.2 g, 0.18 mol) was then charged and the solution was stirred for a further 30 min at 60° C.

The solution was transferred to a heated separating funnel where it was allowed to separate into two clear phases. The lower substantially aqueous phase was separated (5.0 g), followed by the upper substantially organic phase (49.83 g). By quantitative analysis it was shown that >95% of the potassium salt of 6-trifluoromethyl-2-hydroxypyridine was extracted into the organic cyclohexanone phase.

EXAMPLE 6

This example illustrates the extraction of the potassium salt of 6-trifluoromethyl-2-hydroxypyridine from an aqueous solution containing added potassium bromide into cyclohexanone at 60° C.

A solution of potassium hydroxide (3.1 g at 95% strength, 0.05 mol), 6-trifluoromethyl-2-hydroxypyridine (7.1 g, 0.04 mol) and potassium bromide (5.2 g, 0.04 mol) in water (7.8 g), was stirred at 60° C. for one hour. Cyclohexanone (17.2 g, 0.18 mol) was then charged and the solution was stirred for a further 30 min at 60° C.

The solution was transferred to a heated separating funnel where it was allowed to separate into two clear phases. The lower substantially aqueous phase was separated (5.4 g), followed by the upper substantially organic phase (40.00 g). By quantitative analysis it was shown that >99% of the potassium salt of 6-trifluoromethyl-2-hydroxypyridine was extracted into the organic cyclohexanone phase.

EXAMPLE 7

This example illustrates the extraction of the sodium salt of 6-trifluoromethyl-2-hydroxypyridine from an aqueous solution containing added sodium bromide into cyclohexanone at 60° C.

A solution of sodium hydroxide (2.1 g at 95% strength, 0.05 mol), sodium bromide (18.4 g, 0.18 mol) and 6-trifluoromethyl-2-hydroxypyridine (7.1 g, 0.04 mol) in water (7.9 g) stirred at 60° C. for one hour. Cyclohexanone (17.2 g, 0.18 mol) was then charged and the solution was stirred for a further 30 min at 60° C.

The solution was transferred to a heated separating funnel where it was allowed to separate into two clear phases. The lower substantially aqueous phase was separated (9.5 g), followed by the upper substantially organic phase (28.45 g). Qualitative GC analysis showed that the cyclohexanone solution contained 15.4 area % of the sodium salt of 6-trifluoromethyl-2-hydroxypyridine, and that its theoretical yield, calculated from the mass recovered (assuming 15% water content in the cyclohexanone phase), was 94%.

EXAMPLE 8

This is a further example illustrating the extraction of the potassium salt of 6-trifluoromethyl-2-hydroxypyridine from an aqueous solution containing added potassium fluoride into cyclohexanone at 60° C.

6-Trifluoromethyl-2-hydroxypyridine (10 g, 0.0613 mol), aqueous potassium hydroxide solution (8.6 g@50% w/w, 0.076 mol) and water (5.7 g, 0.316 mol) were charged to a stirred flask and heated to 60° C. The mixture was held at this temperature for 1 hour, then potassium fluoride (3.6 g, 0.062 mol) was added and stirred for a further 15 minutes. Cyclohexanone (26.4 g, 0.269 mol) was then added, and stirred at 60° C. for 30 minutes. Two layers were formed, which were separated at 60° C.

8.8 g Of substantially aqueous phase and 43.1 g of substantially organic phase were recovered. (0.9 g of interface was also present.) The organic phase contained 12.2% water (by Karl Fischer titration), 52.4% cyclohexanone (by GC) and 28.4% of the potassium salt of the 6-trifluoromethyl-2-hydroxypyridine (by titration with HCl), indicating that >99% of the salt had been extracted into the cyclohexanone phase.

The analytical method and calculation used are described below.

A sample of the extracted metal salt in solvent (~0.5 g) was accurately weighed and dissolved in deionised water (50 ml). A standardised 1% solution of potassium hydroxide (1 ml) was then added and the solution titrated with a 0.1M solution of hydrochloric acid. The results are analysed as below for Example 1.

$$\text{Salt content (\%)} = \frac{(EP2 - EP1) \times C32 \times C02}{C00 \times 100}$$

EP1 volume of hydrochloric acid added to first endpoint
EP2 volume of hydrochloric acid added to second endpoint
C00 sample weight
C02 molecular weight of salt
C32 strength correction factor for hydrochloric acid
where:
    EP1=0.061 ml
    EP2=6.681 ml
    C00=0.4871 g
    C02=201
    C32=1.0267

$$\text{Salt content (\%)} = \frac{1366.1}{48.17} = 28.4\%$$

EXAMPLE 9

This example illustrates the extraction of the potassium salt of 6-chloro-2-hydroxypyridine from an aqueous solution containing added potassium fluoride into cyclohexanone at 60° C.

6-Chloro-2-hydroxypyridine (5.6 g, 0.0422 mol), aqueous potassium hydroxide solution (5.9 g@50% w/w, 0.052 mol) and water (3.9 g, 0.216 mol) were charged to a stirred flask and heated to 60° C. The mixture was held at this temperature for 1 hour, then cyclohexanone (18.2 g, 0.185 mol) was added and stirred for 15 minutes. Potassium fluoride (2.5 g, 0.042 mol) was then added, and stirred at 60° C. for a further 30 minutes. Two layers were formed, which were separated at 60° C.

4.8 g Of substantially aqueous phase and 29.4 g of substantially organic phase were recovered. The organic phase contained 15.9% water (by Karl Fischer titration), 51.1% cyclohexanone (by GC) and 25.2% of the 6-chloro-2-hydroxypyridine potassium salt (by titration with HCl), indicating that >99% of the salt had been extracted into the cyclohexanone phase.

EXAMPLE 10

This example illustrates the extraction of the potassium salt of 6-difluoromethyl-2-hydroxypyridine from an aqueous solution containing added potassium fluoride produced in situ into cyclohexanone at 60° C.

Potassium hydroxide (0.35 g@50% w/w, 0.00174 mol) and water (0.2 g, 0.011 mol) were charged to a 5 ml flask and heated to 95° C. 6-Difluoromethyl-2-fluoropyridine (0.1947 g, 0.00132 mol) was added and stirred at 95° C. for 105 minutes. The solution was then cooled to 60° C. Cyclohexanone (0.6 g, 0.006 mol) was added and stirred at 60° C. for 30 minutes. The layers were then separated at 60° C.

0.2 g Of substantially aqueous phase and 0.7 g of substantially organic phase were recovered. Titration of the organic phase with HCl indicated that 16.7% w/w was the potassium salt of 6-difluoromethyl-2-hydroxypyridine, indicating that approximately 48% of the salt had been extracted into the cyclohexanone phase.

EXAMPLE 11

This example illustrates the extraction of the potassium salt of 5-trifluoromethyl-2-hydroxypyridine from an aqueous solution containing added potassium fluoride into cyclohexanone at 60° C.

Potassium hydroxide (0.4 g@50% w/w, 0.004 mol) and water (0.3 g, 0.011 mol) were charged to a 5 ml flask and heated to 60° C. 5-Trifluoromethyl-2-hydroxypyridine (0.5 g, 0.00307 mol) was added and stirred at 60° C. for 60 minutes. Potassium fluoride (0.18 g, 0.00307 mol) was added and stirred for 15 minutes, then cyclohexanone (1.32 g, 0.0135 mol) was added and stirred at 60° C. for 30 minutes. The layers were then separated at 60° C.

0.5 g Of substantially aqueous phase and 1.8 g of substantially organic phase were recovered. Titration of the organic phase with HCl indicated that 19.2% w/w was the potassium salt of 5-trifluoromethyl-2-hydroxypyridine, indicating that approximately 56% of the salt had been extracted into the cyclohexanone phase.

EXAMPLE 12

This example illustrates the extraction of the potassium salt of 6-trifluoromethyl-2-hydroxypyridine from an aqueous solution containing added potassium fluoride into diethyl ether at ambient temperature.

Aqueous potassium hydroxide solution (10.0 g@50% w/w, 0.089 mol) and water (6.7 g, 0.372 mol) and 6-trifluoromethyl-2-hydroxypyridine (11.2 g, 0.068 mol), were charged to a stirred flask and heated to 60° C. The mixture was held at this temperature for 1 hour, then potassium fluoride (3.9 g, 0.067 mol) was added and stirred for a further 15 minutes. The reaction mixture was allowed to cool to ambient temperature before adding diethyl ether (22.8 g, 0.3 mol), and stirred at ambient temperature for 30 minutes. Two layers were formed, which were separated at ambient temperature.

6.6 g Of substantially aqueous phase and 42.2 g of substantially organic phase were recovered. The organic phase contained 24.6% water (by Karl Fischer titration) and 35.1% of the potassium salt of the 6-trifluoromethyl-2-hydroxypyridine (by titration with HCl), indicating that the salt had been extracted into the ether phase.

EXAMPLE 13

This example illustrates the extraction of the potassium salt of 6-trifluoromethyl-2-hydroxypyridine from an aqueous solution containing added potassium fluoride into 2-methyl-1-propanol at 60° C.

Aqueous potassium hydroxide solution (10.0 g@50% w/w, 0.089 mol) and water (6.7 g, 0.372 mol) and 6-trifluoromethyl-2-hydroxypyridine (11.2 g, 0.068 mol), were charged to a stirred flask and heated to 60° C. The mixture was held at this temperature for 1 hour, then potassium fluoride (3.9 g, 0.067 mol) was added and stirred for a further 15 minutes. 2-methyl-1-propanol (22.4 g, 0.3 mol)

and was then added, and stirred at 60° C. for 30 minutes. Two layers were formed, which were separated at 60° C.

10.9 g Of substantially aqueous phase and 41.1 g of substantially organic phase were recovered. The organic phase contained 16.4% water (by Karl Fischer titration) and 34.8% of the potassium salt of the 6-trifluoromethyl-2-hydroxypyridine (by titration with HCl), indicating that the salt had been extracted into the 2-methyl-1-propanol phase

EXAMPLE 14

This example illustrates the extraction of the potassium salt of 6-trifluoromethyl-2-hydroxypyridine from an aqueous solution containing added potassium fluoride into n-butanol at 60° C.

Aqueous potassium hydroxide solution (10.0 g@50% w/w, 0.089 mol) and water (6.7 g, 0.372 mol) and 6-trifluoromethyl-2-hydroxypyridine (11.2 g, 0.068 mol), were charged to a stirred flask and heated to 60° C. The mixture was held at this temperature for 1 hour, then potassium fluoride (3.9 g, 0.067 mol) was added and stirred for a further 15 minutes. n-Butanol (22.4 g, 0.3 mol) and was then added, and stirred at 60° C. for 30 minutes. Two layers were formed, which were separated at 60° C.

9.5 g Of substantially aqueous phase and 40.7 g of substantially organic phase were recovered. (1.1 g of interface were also present). The organic phase contained 16.8% water (by Karl Fischer titration) and 33.5% of the potassium salt of the 6-trifluoromethyl-2-hydroxypyridine (by titration with HCl), indicating that approximately 99% of the salt had been extracted into the n-butanol phase.

EXAMPLE 15

This example illustrates the extraction of the potassium salt of 2-hydroxybenzothiazole from an aqueous solution containing added potassium fluoride into cyclohexanone at 60° C.

Potassium hydroxide solution (3.6 g@50% w/w, 0.032 mol) and water (2.4 g, 0.133 mol) were charged to a flask with 2-hydroxybenzothiazole (4.0 g, 0.026 mol) and stirred at 60° C. for 60 minutes. Potassium fluoride (1.5 g, 0.026 mol) was added and stirred at 60° C. for a further 15 minutes. A slurry had formed at this point. Cyclohexanone (11.2 g, 0.114 mol) was then added and stirred at 60° C. for 30 minutes. Two layers were formed and were separated at 60° C.

3.8 g Of substantially aqueous phase and 17.2 g of essentially organic phase were recovered. The organic phase contained 11.4% w/w water (by Karl Fischer titration), 63.3% cyclohexanone (by GC) and 28.2% w/w of the potassium salt of the 2-hydroxybenzothiazole (by titration with HCl), indicating that approximately 98% of the salt had been extracted into the cyclohexanone phase.

EXAMPLE 16

This example illustrates the extraction of the potassium salt of 2-hydroxyquinoline from an aqueous solution containing added potassium fluoride into cyclohexanone at 60° C.

Potassium hydroxide solution (0.8 g@50% w/w, 0.007 mol) and water (1.3 g, 0.072 mol) were charged to a flask with 2-hydroxyquinoline (0.8 g, 0.005 mol) and stirred at 60° C. for 60 minutes. Cyclohexanone (2.4 g, 0.024 mol) was then added and stirred at 60° C. for 15 minutes, before potassium fluoride (0.3 g, 0.005 mol) was added and stirred at 60° C. for a further 30 minutes. Two layers were formed and were separated at 60° C.

0.5 g Of substantially aqueous phase and 4.2 g of essentially organic phase were recovered. The organic phase contained 28.8% w/w water (by Karl Fischer titration), and 44.9% cyclohexanone (by GC). The weight and water/cyclohexanone composition of the substantially organic layer indicated that the potassium salt of 2-hydroxyquinoline had been successfully extracted into the cyclohexanone phase.

EXAMPLE 17

This example illustrates the extraction of the potassium salt of 6-trifluoromethyl-2-hydroxypyridine from an aqueous solution containing added potassium fluoride into ethyl acetate at 60° C.

Potassium hydroxide (3.1 g@95% w/w, 0.05 mol) and water (7.8 g, 0.43 mol) and 6-trifluoromethyl-2-hydroxypyridine (7.13 g, 0.04 mol), were charged to a stirred flask and heated to 60° C. The mixture was held at this temperature for 1 hour, then potassium fluoride (2.3 g, 0.04 mol) was added and stirred for a further 15 minutes. Ethyl acetate (15.5 g, 0.18 mol) was then added, and stirred at 60° C. for 30 minutes. Two layers were formed, which were separated at 60° C.

6.2 g of substantially aqueous phase and 29.1 g of substantially organic phase were recovered. Qualitative GC showed that the potassium salt of the 6-trifluoromethyl-2-hydroxypyridine had been extracted into the ethyl acetate phase.

EXAMPLE 18

This example illustrates the extraction of the potassium salt of 6-trifluoromethyl-2-hydroxypyridine from an aqueous solution containing added potassium fluoride into 4-methyl-2-pentanone (methyl iso-butyl ketone) at 60° C.

Potassium hydroxide (3.1 g@95% w/w, 0.05 mol) and water (7.8 g, 0.43 mol) and 6-trifluoromethyl-2-hydroxypyridine (7.13 g, 0.04 mol), were charged to a stirred flask and heated to 60° C. The mixture was held at this temperature for 1 hour, then potassium fluoride (2.3 g, 0.04 mol) was added and stirred for a further 15 minutes. Methyl isobutyl ketone (17.6 g, 0.18 mol) was then added, and stirred at 60° C. for 30 minutes. Two layers were formed, which were separated at 60° C.

6.9 g of substantially aqueous phase and 33.1 g of substantially organic phase were recovered. Qualitative GC showed that the potassium salt of the 6-trifluoromethyl-2-hydroxypyridine had been extracted into the organic phase.

EXAMPLE 19

This example illustrates the extraction of the potassium salt of 2-hydroxy-6-trifluoromethylpyridine from an aqueous solution containing added potassium fluoride into cyclopentanone at 60° C.

Potassium hydroxide (3.1 g@95% w/w, 0.05 mol) and water (7.8 g, 0.43 mol) and 6-trifluoromethyl-2-hydroxypyridine (7.13 g, 0.04 mol), were charged to a stirred flask and heated to 60° C. The mixture was held at this temperature for 1 hour, then potassium fluoride (2.3 g, 0.04 mol) was added and stirred for a further 30 minutes. Cyclopentanone (14.7 g, 0.18 mol) was then added, and stirred at 60° C. for 30 minutes. Two layers were formed, which were separated at 60° C.

9.35 g of substantially aqueous phase and 30.7 g of substantially organic phase were recovered. Qualitative GC analysis showed that the potassium salt of the 6-trifluoromethyl-2-hydroxypyridine had been extracted into the cyclopentanone phase.

EXAMPLE 20

This example illustrates the extraction of the potassium salt of 6-trifluoromethyl-2-hydroxypyridine from an aqueous solution containing added potassium fluoride into 2-butanone at 60° C.

Potassium hydroxide (3.1 g@95% w/w, 0.05 mol) and water (7.8 g, 0.43 mol) and 6-trifluoromethyl-2-hydroxypyridine (7.13 g, 0.04 mol), were charged to a stirred flask and heated to 60° C. The mixture was held at this temperature for 1 hour, then potassium fluoride (2.3 g, 0.04 mol) was added and stirred for a further 15 minutes. 2-Butanone (24.6 g, 0.18 mol) was then added, and stirred at 60° C. for 30 minutes. Two layers were formed, which were separated at 60° C.

7.2 g Of substantially aqueous phase and 38.3 g of substantially organic phase were recovered. Qualitative GC indicated that the potassium salt of 6-trifluoromethyl-2-hydroxypyridine had been extracted into the 2-butanone phase.

EXAMPLE 21

This example illustrates the extraction of the potassium salt of 6-trifluoromethyl-2-hydroxypyridine from an aqueous solution containing added potassium fluoride into t-amyl alcohol at 60° C.

Potassium hydroxide (3.1 g@95% w/w, 0.05 mol) and water (7.8 g, 0.43 mol) and 6-trifluoromethyl-2-hydroxypyridine (7.13 g, 0.04 mol), were charged to a stirred flask and heated to 60° C. The mixture was held at this temperature for 1 hour, then potassium fluoride (2.3 g, 0.04 mol) was added and stirred for a further 15 minutes. t-Amyl alcohol (15.5 g, 0.18mol) was then added, and stirred at 60° C. for 30 minutes. Two layers were formed, which were separated at 60° C.

6.56 g of substantially aqueous phase and 29.3 g of substantially organic phase were recovered. Quantitative GC analysis showed the potassium salt of the 6-trifluoromethyl-2-hydroxypyridine into the t-amyl alcohol phase.

EXAMPLE 22

This example illustrates the extraction of the potassium salt of 6-trifluoromethyl-2-hydroxypyridine from an aqueous solution containing added potassium fluoride into 2-methylcyclohexanone at 60° C.

Potassium hydroxide (3.1 g@95% w/w, 0.05 mol) and water (7.8 g, 0.43 mol) and 6-trifluoromethyl-2-hydroxypyridine (7.13 g, 0.04 mol), were charged to a stirred flask and heated to 60° C. The mixture was held at this temperature for 1 hour, then potassium fluoride (2.3 g, 0.04 mol) was added and stirred for a further 15 minutes. 2-Methylcyclohexanone (19.8 g, 0.18 mol) was then added, and stirred at 60° C. for 30 minutes. Two layers were formed, which were separated at 60° C.

5.05 g Of substantially aqueous phase and 35.6 g of substantially organic phase were recovered. Qualitative GC indicated that the potassium salt of 6-trifluoromethyl-2-hydroxypyridine had been extracted into the 2-methylcyclohexanone phase.

EXAMPLE 23

This example illustrates the extraction of the potassium salt of 6-trifluoromethyl-2-hydroxypyridine from an aqueous solution containing added potassium sulphate into cyclohexanone at 60° C.

Potassium hydroxide (3.1 g@95% w/w, 0.05 mol) and water (7.8 g, 0.43 mol) and 6-trifluoromethyl-2-hydroxypyridine (7.13 g, 0.04 mol), were charged to a stirred flask and heated to 60° C. The mixture was held at this temperature for 1 hour, then potassium sulphate (7.03 g, 0.04 mol) was added and stirred for a further 15 minutes. Cyclohexanone (17.2 g, 0.18 mol) was then added, and stirred at 60° C. for 30 minutes. Two layers were formed, which were separated at 60° C.

6.8 g Of substantially aqueous phase and 33.3 g of substantially organic phase were recovered.

The organic phase contained 30.8% water (by Karl Fischer titration). Quantitative GC analysis showed 68% extraction of the potassium salt of 6-trifluoromethyl-2-hydroxypyridine into the cyclohexanone phase.

EXAMPLE 24

This example illustrates the extraction of the potassium salt of 6-trifluoromethyl-2-hydroxypyridine from an aqueous solution containing added potassium phosphate into cyclohexanone at 60° C.

Potassium hydroxide (3.1 g@95% w/w, 0.05 mol) and water (7.8 g, 0.43 mol) and 6-trifluoromethyl-2-hydroxypyridine (7.13 g, 0.04 mol), were charged to a stirred flask and heated to 60° C. The mixture was held at this temperature for 1 hour, then potassium phosphate (8.74 g, 0.04 mol) was added and stirred for a further 15 minutes. Cyclohexanone (17.2 g, 0.18 mol) was then added, and stirred at 60° C. for 30 minutes. Two layers were formed, which were separated at 60° C.

17.3 Of substantially aqueous phase and 28.1 g of substantially organic phase were recovered.

The organic phase contained 18.4% water (by Karl Fischer titration). Qualitative GC analysis showed 38% extraction of the potassium salt of 6-trifluoromethyl-2-hydroxypyridine into the cyclohexanone phase.

EXAMPLE 25

This example illustrates the extraction of the sodium salt of 6-trifluoromethyl-2-hydroxypyridine from an aqueous solution containing added sodium chloride into cyclohexanone at 60° C.

Sodium hydroxide (2.1 g@97% w/w, 0.05 mol) and water (7.9 g, 0.44 mol) and 6-trifluoromethyl-2-hydroxypyridine (7.13 g, 0.04 mol), were charged to a stirred flask and heated to 60° C. The mixture was held at this temperature for 1 hour, then sodium chloride (2.34 g, 0.04 mol) was added and stirred for a further 15 minutes. Cyclohexanone (17.2 g, 0.18 mol) was then added, and stirred at 60° C. for 35 minutes. Two layers were formed, which were separated at 60° C.

9.9 Of substantially aqueous phase and 15.7 g of substantially organic phase were recovered.

Qualitative GC indicated that the potassium salt of 6-trifluoromethyl-2-hydroxypyridine had been extracted into the cyclohexanone phase.

EXAMPLE 26

This example illustrates the extraction of the calcium salt of 6-trifluoromethyl-2-hydroxypyridine from an aqueous solution containing added calcium chloride into cyclohexanone at 60° C.

A solution of calcium hydroxide (97%, 1.6 g, 0.02 mol) and water (21.9 g) was charged to a 3 necked round bottomed flask. 6-Trifluoromethyl-2-hydroxypyridine (71.3%, 10 g, 0.04 mol) was charged and the solution was stirred for one hour at 60° C. Calcium chloride (100%, 2.43 g, 0.02 mol) was charged to the flask and the solution was held for 15 minutes at 60° C. Cyclohexanone (100%, 17.2 g, 0.18 mol) was charged and the solution was stirred for a further 30 minutes at 60° C. Only one phase was present at this time so further calcium chloride (7.2 g, 0.06 mol) was added with stirring until a phase separation was observed. The solution was then transferred to a heated separating funnel where the two phases were allowed to separate. The aqueous phase (33.6 g) was collected followed by the organic phase (22.6 g).

Extraction of the calcium salt of 6-trifluoromethyl-2-hydroxypyridine into the organic phase was shown to have been successful by qualitative GC analysis and as calculated from the mass recovered.

The invention claimed is:

1. A process for extracting from aqueous solution the alkali metal or calcium salt of a halo or haloalkyl substituted 2-hydroxypyridine, or a 2-hydroxyquinoline or 2-hydroxybenzothiazole which comprises contacting an aqueous alkaline or neutral solution of the alkali metal or calcium salt, in which is dissolved an alkali metal fluoride, chloride, bromide, hydroxide, sulphate, sulphite, cyanate, cyanide, thiocyanate, thiosulphate, sulphide, phosphate, hydrogen phosphate, carbonate, bicarbonate, borate, chlorate, hypochlorite, perchlorate, nitrite, chromate, dichromate or permanganate or calcium chloride, bromide, nitrate, nitrite, chlorate, hypochlorite, perchlorate, thiocyanate, thiosulphate, chromate, dichromate or permanganate, with a partially water-miscible organic solvent so as to transfer aqueous solution of the alkali metal or calcium salt of the 2-hydroxypyridine, 2-hydroxyquinoline or 2-hydroxybenzothiazole into the solvent whilst retaining separate aqueous and solvent phases, and thereafter separating the solvent phase containing the alkali metal or calcium salt and water from the aqueous phase, the ratio of solvent to water in the separated solvent phase being from 0.5:1 to 10:1 w/w.

2. A process according to claim 1 in which the ratio of solvent to water in the separated solvent phase is from 0.5:1 to 5:1 w/w.

3. A process according to claim 1 in which the ratio of solvent to water in the separated solvent phase is from 0.5:1 to 3:1 w/w.

4. A process according to any one of claims 1 to 3 in which the solvent is a cycloalkanone.

5. A process according to any one of claims 1 to 3 in which the solvent is a cyclohexanone.

6. A process according to any one of the preceding claims in which the halo or haloalkyl substituted 2-hydroxypyridine is 6-chloro-2-hydroxypyridine, 5-trifluoromethyl-2-hydroxypyridine or 6-difluoromethyl-2-hydroxypyridine.

7. A process according to claim 1 in which the halo or haloalkyl substituted 2-hydroxypyridine is 6-trifluoromethyl-2-hydroxypyridine.

8. A process according to any one of the preceding claims in which the amount of alkali metal fluoride, chloride, bromide, hydroxide, sulphate, sulphite, cyanate, cyanide, thiocyanate, thiosulphate, sulphide, phosphate, hydrogen phosphate, carbonate, bicarbonate, borate, chlorate, hypochlorite, perchlorate, nitrite, chromate, dichromate or permanganate or calcium chloride, bromide, nitrate, nitrite, chlorate, hypochlorite, perchlorate, thiocyanate, thiosulphate, chromate, dichromate or permanganate used is at least 0.5 mole and up to 2 moles for each mole of the alkali metal or calcium salt of the 2-hydroxypyridine, 2-hydroxyquinoline or 2-hydroxybenzothiazole present.

9. A process for extracting from aqueous solution the alkali metal salt of 6-trifluoromethyl-2-hydroxypyridine, which comprises contacting an alkaline aqueous solution of the alkali metal salt, in which is dissolved an alkali metal fluoride, chloride, bromide, sulphate or phosphate, with a cycloalkanone, so as to transfer the alkali metal salt into the cycloalkanone, and thereafter separating the cycloalkanone containing the alkali metal salt from the aqueous solution.

10. A process according to any one of the preceding claims in which the process is carried out at atmospheric pressure at a temperature of from 0° C. to 90° C.

* * * * *

UNITED STATES PATENT AND TRADEMARK OFFICE
CERTIFICATE OF CORRECTION

PATENT NO.         : 7,186,839 B2                                              Page 1 of 1
APPLICATION NO. : 10/332105
DATED              : March 6, 2007
INVENTOR(S)       : Raymond Jones et al.

It is certified that error appears in the above-identified patent and that said Letters Patent is hereby corrected as shown below:

In claim 4, line 1, please replace "according to any one of claims 1 to 3" with --according to claim 1--.

In claim 5, line 1, please replace "according to any one of claims 1 to 3" with --according to claim 1--.

In claim 6, line 1, please replace "according to any one of the preceding claims" with --according to claim 1--.

In claim 8, line 1, please replace "according to any one of the preceding claims" with --according to claim 1--.

In claim 10, line 1, please replace "according to any one of the preceding claims" with --according to claim 1--.

Signed and Sealed this

Sixteenth Day of September, 2008

JON W. DUDAS
*Director of the United States Patent and Trademark Office*